United States Patent [19]

Meier

[11] Patent Number: 5,082,952
[45] Date of Patent: Jan. 21, 1992

[54] PROCESS FOR THE PREPARATION OF METALLOCENE COMPLEXES

[75] Inventor: Kurt Meier, Allschwil, Switzerland

[73] Assignee: Ciba-Geigy Corporation, Ardsley, N.Y.

[21] Appl. No.: 867,113

[22] Filed: May 27, 1986

[30] Foreign Application Priority Data

Jun. 6, 1985 [CH] Switzerland ............... 2397/85

[51] Int. Cl.$^5$ ............................................. C07F 17/02
[52] U.S. Cl. ............................ 549/3; 548/402; 549/209; 556/7; 556/14; 556/143; 556/145; 546/4
[58] Field of Search ............... 548/402; 549/3, 206; 556/143

[56] References Cited

U.S. PATENT DOCUMENTS

| 2,791,597 | 5/1957 | Anzilotti et al. | 556/143 |
| 3,130,214 | 4/1964 | Coffield et al. | 556/46 |
| 4,624,912 | 11/1986 | Zweifel et al. | 430/258 |

FOREIGN PATENT DOCUMENTS 94915 6/1983 European Pat. Off. .

OTHER PUBLICATIONS

Mueherties et al., J. Organometallic Chem. 178, 197 (1979).
Draggett et al., J. Organometallic Chem. 135, C60 (1977).
H. Schumann, Chemiker Zeitung 108, pp. 239-251 (1984).
Chem. Abst. 84, 5119q (1976) Nesmeyamov.
Chem. Abst. 80, 37251k (1974) Nesmeyamov.
Chem. Abst. 69, 2994a (1968) Yuk'yanets.
Organic Chemistry (4th ed.) 1980, p. 40, Pire et al.

Primary Examiner—Mark L. Berch
Attorney, Agent, or Firm—Harry Falber

[57] ABSTRACT

The invention relates to a process for the preparation of $\pi$-arene-iron complexes of the general formula I $$[R^1(R^2Fe^{II})_a]_b^{+a} (LQ_m)^{-b} \qquad (I)$$

wherein
  a is 1 or 2,
  b is an integer from 1 to 3,
  m is an integer corresponding to the valency of L+b,
  L is a divalent to heptavalent metal or non-metal,
  Q is a halogen atom,
  $R^1$ is a $\pi$-arene, an O- or S-heteroarene or a pyrrole or an indole and
  $R^2$ is a cyclopentadienyl anion or an indenyl anion.

The $\pi$-arene-iron complexes of formula I are obtained by ligand exchange at elevated temperatures from $\pi$-arene-iron complexes of formula II $$[R^3(R^2Fe^{II})_a]_b^{+a} (LQ_m)_a^{-b} \qquad (II)$$

wherein $R^3$ is a condensed $\pi$-arene which differs from $R^1$. The $\pi$-arene-iron complexes of formula I are suitable as photoinitiators for curable compositions containing cationically polymerizable organic materials.

11 Claims, No Drawings

PROCESS FOR THE PREPARATION OF METALLOCENE COMPLEXES

The present invention relates to a novel process for the preparation of π-arene-iron complexes by means of ligand exchange under the influence of heat and using cyclopentadienyl-π-arene-iron complexes or indenyl-π-arene-iron complexes in which the π-arene is a condensed π-arene. Throughout this specification, the expression π-arene-iron complex shall be used as a general term for iron complexes containing a π-arene and an anion of a π-arene as ligands.

It is known from published European patent application 94 915 that it is possible to exchange ligands of metallocene complexes in the presence of a Lewis acid and thereby to obtain chemically different metallocenes.

π-Arenes which are sensitive to Lewis acids can not be introduced into metallocenes in this manner, and it is also impossible to employ as educt metallocene complexes which are labile to Lewis acids.

Further, it is known from H. Schumann, Chemiker Zeitung 108, pp. 239-251 (1984) that the [cyclopentadienyl-Fe(p-xylene)]PF$_6$ complex is capable of photochemically exchanging p-xylene for other arenes. Complexes containing condensed aromatic compounds can not be prepared by this method since the final products—especially in solution—are very photolabile. Moreover, the yields of π-arene iron complexes which can be affored by this process are low and, furthermore, the use of light energy is expensive and uneconomical.

It is desirable to provide a ligand exchange process in which neither Lewis acids nor light energy have to be used.

Accordingly, the present invention relates to a process for the preparation of complexes of the general formula I

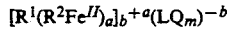

$$[R^1(R^2Fe^{II})_a]_b^{+a}(LQ_m)^{-b} \qquad (I)$$

wherein
a is 1 or 2,
b is an integer from 1 to 3,
m is an integer corresponding to the valency of L+b,
L is a divalent to heptavalent metal or non-metal,
Q is a halogen atom,
$R^1$ is a π-arene, an O- or S-heteroarene or a pyrrole or an indole and
$R^2$ is a cyclopentadienyl anion or an indenyl anion,
which process comprises reacting a complex of formula II

$$[R^3(R^2Fe^{II})_a]_b^{+a}(LQ_m)_a^{-b} \qquad (II)$$

wherein a, b, m, L, Q and $R^2$ are as defined above and $R^3$ is a condensed π-arene, with a π-arene $R^1$ which differs from $R^3$ or with an O- or S-heteroarene or a pyrrole or an indole $R^1$, at a temperature of at least 60° C.

Possible π-arenes or O- or S-heteroarenes $R^1$ are, in particular, aromatic hydrocarbon compounds containing 6 to 24 carbon atoms or oxygen- or sulfur-containing heteroaromatic compounds containing 4 to 20 carbon atoms, which compounds may be unsubstituted or mono- or polysubstituted by identical or different radicals such as $C_1$–$C_8$alkyl, $C_2$–$C_6$alkylene which is attached in the ortho-position to the π-arene or to the O- or S-heteroarene, one or two carbon atoms, preferably one carbon atom, of which alkylene group may be replaced by O or S atoms, or $C_1$–$C_8$alkoxy, hydroxy, hydroxy-$C_1$–$C_8$alkyl, $C_1$–$C_8$alkylthio, carbo-$C_1$–$C_8$alkoxy-$C_1$–$C_3$alkyl or $C_1$–$C_8$alkenyl.

The alkyl, alkylene, heteroalkylene, alkoxy, hydroxyalkyl, alkylthio, carboalkoxyalkyl or alkenyl substituents may be straight chain or branched.

Example of alkyl, alkylene, heteroalkylene, alkoxy, hydroxyalkyl, alkylthio, carboalkoxyalkyl and alkenyl substituents are methyl, ethyl, n-propyl, isopropyl, n-butyl, sec-butyl, tert-butyl, n-pentyl, n-hexyl and n-octyl, 1,2-ethylene, 1,3-propylene, 2,4-butylene, 1-methyl-1,4-butylene, 2-methyl-1,4-butylene, 1,5-pentamethylene and 1,6-hexamethylene, 2-oxa-1,3-propylene, 2-oxa-1,4-butylene, 1-oxa-1,4-butylene, 1-thia-1,4-butylene, 1,4-dioxa-1,4-butylene, 1,4-dithia-1,4-butylene and 3-oxa-1,5-pentamethylene, methoxy, ethoxy, n-propoxy, isopropoxy, n-butoxy, n-hexyloxy and n-octyloxy, hydroxymethyl, 1-hydroxyeth-2-yl, 1-hydroxyeth-1-yl, 2-hydroxyprop-2-yl, 1-hydroxyprop-3-yl, 1-hydroxybut-4-yl, 1-hydroxypent-5-yl, 1-hydroxyhex-6-yl and 1-hydroxyoct-8-yl, methylthio, ethylthio, n-propylthio, isopropylthio, n-butylthio, n-hexylthio and n-octylthio, carbomethoxymethyl, carboethoxymethyl, carbopropoxymethyl, carboisopropoxymethyl, carbo-n-butoxymethyl, carbo-n-pentoxymethyl, carbo-n-hexyloxymethyl, carbo-n-octyloxymethyl, carbomethoxyethyl, carboethoxyethyl, carbomethoxypropyl and carboethoxypropyl, vinyl, allyl, 1- or 2-methylvinyl, butenyl, pentenyl, hexenyl and octenyl.

Preferred substituted arenes $R^1$ are those which contain one or two of the above-mentioned substituents, in particular methyl, ethyl, hydroxy, methoxy, ethoxy, carbomethoxymethyl or carboethoxymethyl.

The π-arenes or O- or S-heteroarenes $R^1$ may be mononuclear, condensed polynuclear or uncondensed polynuclear systems, in which last named systems the nuclei may be linked together direct and/or through bridge members such as $C_1$–$C_4$alkylene, $C_2$–$C_8$alkylidene, $C_5$–$C_8$cycloalkylidene, —CO—, —SO—, —SO$_2$— and —SiR$_2$—, wherein R is phenyl, $C_1$–$C_4$alkyl or $C_2$–$C_6$alkenyl.

$R^1$ as π-arene may have up to 6 nuclei and is preferably a mono-, bi- or trinuclear system.

$R^1$ as an O- or S-heteroarene is preferably a mononuclear or a condensed bi- or trinuclear system containing 1 or 2 hetero atoms. Systems containing one hetero atom are particularly preferred.

$R^1$ as mononuclear π-arene or O- or S-heteroarene preferably contains 5 or 6 ring members.

Examples of suitable groups $R^1$ are benzene, toluene, xylenes, ethylbenzene, methoxybenzene, ethoxybenzene, dimethoxybenzene, trimethylbenzene, naphthalene, 1,2-dihydronaphthalene, 1,2,3,4-tetrahydronaphthalene, methylnaphthalenes, methoxynaphthalenes, ethoxynaphthalenes, biphenyl, terphenyl, stilbene, indene, indan, hydroxyindans, methoxyindans, fluorene, phenanthrene, anthracene, 9,10-dihydroanthracene, triphenylene, thiophene, furan, benzothiophene, benzofuran, chromene, xanthene, thioxanthene, naphthothiophene, thianthrene, biphenyl oxide and biphenyl sulfide.

The pyrrole or indole may be substituted in the same manner as the π-arene $R^1$, preferably at the carbon atoms. The nitrogen atom is preferably substituted by alkyl, in particular $C_1$–$C_4$alkyl.

$R^2$ in formulae I and II is a cyclopentadienyl anion or an indenyl anion, which anions may be substituted by identical or different radicals such as $C_1$–$C_8$alkyl or $C_1$–$C_8$alkoxy.

Examples of substituents at the cyclopentadienyl or indenyl anion $R^2$ are methyl, ethyl, n-propyl, isopropyl, n-butyl, sec-butyl, tert-butyl, n-pentyl, n-hexyl and n-octyl, methoxy, ethoxy, n-propoxy, isopropoxy, n-butoxy, n-hexyloxy and n-octyloxy.

Preferred substituted cyclopentadienyl anions or indenyl anions $R^2$ are those containing one substituent, in particular a methyl or methoxy group.

In a particularly preferred embodiment of the process, $R^2$ is an unsubstituted cyclopentadienyl anion.

$R^3$ as condensed $\pi$-arene preferably contains 10 to 24 carbon atoms and may be unsubstituted or mono- or polysubstituted by e.g. $C_1$–$C_8$alkyl or $C_1$–$C_8$alkoxy groups.

Examples of substituents at the condensed $\pi$-arene $R^3$ are methyl, ethyl, n-propyl, isopropyl, n-butyl, sec-butyl, tert-butyl, n-pentyl, n-hexyl and n-octyl, methoxy, ethoxy, n-propoxy, isopropoxy, n-butoxy, n-hexyloxy and n-octyloxy.

Preferred substituted condensed $\pi$-arenes $R^3$ are those containing one or two of the above-mentioned substituents, in particular methyl or methoxy.

Examples of suitable condensed $\pi$-arenes $R^3$ are naphthalene, methylnaphthalenes, methoxynaphthalenes, ethoxynaphthalenes, phenanthrene, anthracene, pyrene, naphthacene, coronene or perylene.

$R^3$ is preferably naphthalene, 1- or 2-methylnaphthalene, 1- or 2-methoxynaphthalene, or pyrene.

Each of a and b in formulae I and II is, independently of the other, preferably the value 1.

Examples of suitable metals and non-metals L are Sb, B, P, As, Fe, Sn, Bi, Al, Ga, In, Ti, Zr, Sc, V, Cr, Mn and Cu; lanthanides such as Ce, Pr and Nd or actinides such as Th, Pa, U or Np.

L is preferably P, As, B or Sb, with P being particularly preferred.

Q as a halogen atom is preferably F, Cl or Br, with F being particularly preferred.

Examples of complex anions $[LQ_m]^{-b}$ are $BF_4^-$, $[B(phenyl)_4]^-$, $PF_6^-$, $AsF_6^-$, $SbF_6^-$, $FeCl_4^-$, $SnCl_6^{2-}$, $SbCl_6^-$ and $BiCl_6^-$. Particularly preferred complex anions $[LQ_m]^{-b}$ are $SbF_6^-$, $AsF_6^-$, $BF_4^-$, $[B(phenyl)_4]^-$ and $PF_6^-$, with $BF_4^-$ and $PF_6^-$ being most preferred.

The reaction is preferably carried out at a temperature of at least 90° C., and the reaction times may be from hours to days. The upper temperature limit is determined by the stability of the metallocene complex. However, in general, temperatures of not more than 250° C., preferably not more than 200° C., are applied. It is particularly preferred to carry out the reaction in a temperature range from 90° to 130° C.

The process can be carried out without the addition of a solvent, e.g. in the melt, or it can, however, be carried out using an inert solvent, in which case a suitable inert solvent is an excess of the $\pi$-arene $R^1$ or an aprotic solvent. Examples of suitable aprotic solvents are branched and unbranched aliphatic or cycloaliphatic hydrocarbons such as n-heptane, n-octane, n-decane, n-undecane, n-dodecane, isooctane, cyclohexane, cycloheptane, cyclooctane or mixtures of different aliphatic and/or cycloaliphatic hydrocarbons (ligroin), halogenated hydrocarbons such as 1,2-dichloroethane, 1,1,1-trichloroethane, 1,1,2,2-tetrachloroethane, 1,2-dichloropropane, glycol ethers of the general formula $R^4$—O—$(CH_2)_n$—O—$R^4$, wherein n is 2 to 6 and $R^4$ is $C_1$–$C_4$alkyl, in particular methyl or ethyl, e.g. ethylene glycol dimethyl ether or ethylene glycol diethyl ether, polyalkylene glycol diethers of the formula $R^4$—O$(C_nH_{2n}$—O$\frac{}{x}R^4$, wherein $R^4$ is $C_1$–$C_4$alkyl, in particular methyl or ethyl, n is 2 to 6, preferably 2 to 4, and x is 2 to 4, e.g. diethylene glycol dimethyl ether or triethylene glycol dimethyl ether. It is preferred to use as solvents halogenated hydrocarbons or an excess of the $\pi$-arene $R^1$.

Surprisingly, in the process of this invention the ligand exchange can be effected by merely heating the components and without the addition of Lewis acids, which, compared with known processes, represents a simplification of the preparation of $\pi$-arene-iron complexes. In particular, the hydrolytic working up of the reaction mixture in order to separate the Lewis acid catalyst can be dispensed with as a process step. Ecologically, this is particularly advantageous. Moreover, higher yields can be obtained.

A further advantage resides in the fact that the process of this invention provides access to a series of novel cyclopentadienyl-$\pi$-arene-iron complexes and indenyl-$\pi$-arene-iron complexes which, as is the case with e.g. thiophene, on account of the sensitivity of the reactants or substituents to Lewis acids have not so far been obtainable.

The $\pi$-arene-iron complexes of formula I are suitable e.g. as photoinitiators for curable compositions containing cationically polymerisable organic materials, as is described in published Europen patent application 94 915.

The invention is illustrated in more detail by the following Examples.

EXAMPLE 1

In a 50 ml three-necked round flask, 10 g (24.5 mmol) of ($\eta^6$-1-methylnaphthalene)($\eta^5$-cyclopentadienyl)iron(II) hexafluorophosphate and 6 g (40 mmol) of 5-methoxyindan are heated, under inert gas, for 2½ hours at 130° C. After the dark solution has cooled, it is diluted with 50 ml of methylene chloride, and hexane is then added until the onset of crystallisation. The yield is 9.66 g (95.2%) of ($\eta^6$-5-methoxyindan)($\eta^5$-cyclopentadienyl)iron(II) hexafluorophosphate in the form of yellow crystals with a melting point of 122°–124° C.

EXAMPLES 2 TO 8

In a 25 ml bomb tube, 5 mmol of starting complex ($R^3$Fe-cyclopentadienyl) $PF_6$, 5 mmol of the ligand $R^1$ to be introduced and 5 ml of 1,2-dichloroethane are heated at 120° C. Working up is as described in Example 1. The other reaction conditions and the results are listed in the following Table 1.

TABLE 1

| | | ($R^3$Fe-Cyclopentadienyl)$PF_6$ + $R^1 \rightarrow$ ($R^1$Fe-Cyclopentadienyl)$PF_6$ | | | |
|---|---|---|---|---|---|
| Ex. | $R^3$ | $R^1$ | Reaction time | Yield | Melting point |
| 2 | 1-methylnaphthalene | stilbene | 4 h | 77.5% | 165–168° C. |
| 3 | 1-methylnaphthalene | thiophene | 2 h | 61.4% | 184° C. |

TABLE 1-continued (R³Fe-Cyclopentadienyl)PF₆ + R¹→(R¹Fe-Cyclopentadienyl)PF₆

| Ex. | R³ | R¹ | Reaction time | Yield | Melting point |
|---|---|---|---|---|---|
| 4 | naphthalene | toluene | 14 h | 88.1% | 165° C. |
| 5 | 1-methylnaphthalene | ethyl phenylacetate | 3 h | 49.0% | 102° C. |
| 6 | 1-methylnaphthalene | 3,5-dicarbomethoxy-2,6-dimethyl-4-phenyl-1,4-dihydropyridine | 3 h | 59.0% | 216° C. (decomp.) |
| 7 | 1-methylnaphthalene | 9-benzylanthracene | 3 h | 78.0% | 245° C. (decomp.) |
| 8 | 1-methylnaphthalene | 1-methylpyrrole | 3 h | 25.0% | 125–130° C. (decomp.) |

EXAMPLES 9 TO 11

In a 100 ml sulfurating flask, 5 mmol of starting complex $[(R_3Fe\text{-cyclopentadienyl})+](LQ_m)^{-b}$, 5 mmol of the ligand $R^1$ to be introduced and 30 ml of 1,2-dichloropropane are heated under reflux (T=95° C.). Working up is as described in Example 1. The other reaction conditions and the results are listed in the following Table 2.

TABLE 2

(R³Fe-Cyclopentadienyl)⁺ (LQ_m)⁻ᵇ + R¹→(R¹Fe-Cyclopentadienyl)⁺⁰ (LQ_m)⁻ᵇ

| Ex. | R³ | (LQ_m)⁻ᵇ | R¹ | Reaction time | Yield | Melting point |
|---|---|---|---|---|---|---|
| 9 | pyrene | PF₆⁻ | 2-methoxynaphthalene | 24 h | 85.0% | 126–130° C. |
| 10 | 1-methylnaphthalene | PF₆⁻ | 5-hydroxyindan | 24 h | 37.5% | 165–170° C. |
| 11 | 1-methylnaphthalene | BF₄⁻ | stilbene | 24 h | 52.5% | 140–141° C. |

What is claimed is:

1. The process which comprises allowing a first complex of the formula $$[R^3R^2Fe^{II}]^+(LF_m)^-$$

in which
R² is the cyclopentadienyl anion;
R³ is naphthalene, phenanthrene, anthracene or pyrene, unsubstituted or substituted with methyl or methoxy; and $(LF_m)^-$ is $SbF_6^-$, $BF_4^-$, $AsF_6^-$, or $PF_6^-$;

to react with a compound R¹ at a temperature of at least 60° C. without addition of a Lewis acid to produce a second complex of the formula $$[R^1R^2Fe^{II}]^+(LF_m)^-$$

in which R² and $(LF_m)^-$ are as defined for said first complex and R¹ is a ligand-forming cyclic compound different from R³ and selected from the group consisting of benzene, toluene, xylene, methoxybenzene, naphthalene, methoxynaphthalene, methylnaphthalene, biphenyl, indan, hydroxyindan, methoxyindan, indene, stilbene, thiophene, furan, and benzothiophene.

2. The process according to claim 1 wherein the reaction is carried out in the presence of an inert aprotic solvent or excess R³.

3. The process which comprises heating a first complex of the formula:

$$[R^3(R^2Fe^{II})_a]_b^{+a}(LF_m)^{-b}$$

wherein
R² is a cyclopentadienyl or an indenyl anion;
R³ is a hydrocarbon containing at least two condensed aromatic rings and from 10 to 24 ring carbon atoms, said hydrocarbon being unsubstituted or substituted with one or more substituents independently selected from the group consisting of alkyl of 1 to 8 carbon atoms, alkoxy of 1 to 8 carbon atoms, alkylthio of up to 8 carbon atoms, hydroxyalkyl of up to 8 carbon atoms, alkenyl of up to 8 carbon atoms, or alkyl of up to 3 carbon atoms substituted with carbalkoxy of up to 8 carbon atoms in the alkoxy group;
L is a divalent to heptavalent metal or non metal selected from the group consisting of antimony, boron, phosphorous, arsenic, iron, tin, bismuth, aluminum, gallium, indium, titanium, zirconium, scandium, vanadium, chromium, manganese, and copper;
a has a value of 1 or 2;
b has a value of 1, 2, or 3; and
m is the sum of b plus the valency of L;
with a compound R¹ at a temperature of at least 60° C. without addition of a Lewis acid to produce a second complex of the formula:

$$[R^1(R^2Fe^{II})_a]_b^{+a}(LF_m)^{-b}$$

in which
R², L, a, b, and m are as defined for said first complex; and
R¹ is a ligand-forming cyclic compound different from R³ and in which the cyclic structure is selected from the group consisting of (i) an aromatic hydrocarbon ring system of 6 to 24 ring carbon atoms;
(ii) a nitrogen containing ring system selected from the group consisting of pyrrole and indole; and
(iii) a heteroaromatic ring system containing 4 to 20 ring carbon atoms and at least one hetero ring atom selected from the group consisting of oxygen and sulfur, said aromatic and heteroaromatic ring systems being monocyclic, fused, or linked through a carbon-carbon bond or a linking member selected from the group consisting of alkylene of 1 to 4 carbon atoms, alkylidene of 2 to 8 carbon atoms, cycloalkylene of 5 to 8 carbon atoms, —CO—, —SO—, —SO$_2$— and —SiR$_2$— where R is phenyl, alkyl of 1 to 4 carbon atoms, or alkenyl of 2 to 6 carbon atoms; and said cyclic structure being (a) unsubstituted,
(b) substituted on one or more ring carbon atoms with substituents selected from the group consisting of hydroxy, alkyl of 1 to 8 carbon atoms, alkoxy of 1 to 8 carbon atoms, alkylthio of up to 8 carbon atoms, hydroxyalkyl of up to 8 carbon atoms, alkenyl of up to 8 carbon atoms, or alkyl of up to 3 carbon atoms substituted with carbalkoxy of up to 8 carbon atoms in the alkoxy group, or
(c) bridged between two vicinal ring carbon atoms with alkylene of 2 to 6 carbon atoms, one carbon atom of which alkylene may be replaced with oxygen or sulfur.

4. A process according to claim 3, wherein a is 1 and $R^1$ is benzene, toluene, xylene, methoxybenzene, naphthalene, methoxynaphthalene, methylnaphthalene, biphenyl, indan, hydroxyindan, methoxyindan, indene, stilbene, thiophene, furan or benzothiophene.

5. A process according to claim 3, wherein the reaction is carried out in the melt.

6. A process according to claim 3, wherein $R^3$ is mono- or polysubstituted by $C_1$-$C_8$alkyl or $C_1$-$C_8$alkoxy groups.

7. A process according to claim 3, wherein $R^3$ is naphthalene, 1- or 2-methylnaphthalene, 1- or 2-methoxynaphthalene, phenanthrene, anthracene or pyrene.

8. A process according to claim 3, wherein $R^2$ is a cyclopentadienyl anion which is unsubstituted or mono- or polysubstituted by $C_1$-$C_8$alkyl or $C_1$-$C_8$alkoxy groups.

9. A process according to claim 3, wherein $(LF_m)^{-b}$ is one of the complex anions $SbF_6^-$, $BF_4^-$, $AsF_6^-$ or $PF_6^-$.

10. A process according to claim 3, wherein the reaction is carried out in the presence of an inert aprotic solvent.

11. A process according to claim 3, wherein the solvent is $R^3$.

* * * * *